United States Patent
Cho et al.

(10) Patent No.: US 10,206,969 B2
(45) Date of Patent: Feb. 19, 2019

(54) PEPTIDE FOR PREVENTING OR TREATING INFLAMMATORY DISEASES AND USE THEREOF

(71) Applicant: BIO PEP CO., LTD., Seoul (KR)

(72) Inventors: Dae Ho Cho, Seoul (KR); Kyung Eun Kim, Seoul (KR); Sun Young Park, Yongin-si (KR); Myung Jin Jung, Seoul (KR); Joo Hyun Lee, Goyang-si (KR)

(73) Assignee: BIO PEP CO., LTD., Seoul (KR)

( * ) Notice: Subject to any disclaimer, the term of this patent is extended or adjusted under 35 U.S.C. 154(b) by 0 days.

(21) Appl. No.: 15/739,942

(22) PCT Filed: Feb. 27, 2017

(86) PCT No.: PCT/KR2017/002116
§ 371 (c)(1),
(2) Date: Dec. 26, 2017

(87) PCT Pub. No.: WO2017/155233
PCT Pub. Date: Sep. 14, 2017

(65) Prior Publication Data
US 2018/0185436 A1    Jul. 5, 2018

(30) Foreign Application Priority Data

Mar. 9, 2016  (KR) .................. 10-2016-0028227
Oct. 17, 2016  (KR) .................. 10-2016-0134176

(51) Int. Cl.
| | |
|---|---|
| A61K 38/08 | (2006.01) |
| A23L 33/18 | (2016.01) |
| A61P 37/06 | (2006.01) |
| A61P 29/00 | (2006.01) |
| A61K 47/64 | (2017.01) |

(52) U.S. Cl.
CPC .............. *A61K 38/08* (2013.01); *A23L 33/18* (2016.08); *A61K 47/64* (2017.08); *A61P 29/00* (2018.01); *A61P 37/06* (2018.01)

(58) Field of Classification Search
None
See application file for complete search history.

(56) References Cited

U.S. PATENT DOCUMENTS

| | | | |
|---|---|---|---|
| 2003/0232014 A1* | 12/2003 | Burke | ................. A61K 51/088 424/1.69 |
| 2004/0078842 A1* | 4/2004 | Zilberstein | ............. A01N 63/00 800/279 |
| 2014/0256681 A1 | 9/2014 | Desai | |
| 2015/0299252 A1 | 10/2015 | Eggink et al. | |

FOREIGN PATENT DOCUMENTS

| | | |
|---|---|---|
| CN | 1872873 A | 12/2006 |
| CN | 103739670 A | 4/2014 |
| JP | 07-025783 A | 1/1995 |
| JP | 2013-513657 A | 4/2013 |

OTHER PUBLICATIONS

Korean Intellectual Property Office. International Search Report—PCT/KR2017/002116. dated Jun. 2, 2017.*
Korean Intellectual Property Office. Written Opinion—PCT/KR2017/002116. dated Jun. 2, 2017.*

* cited by examiner

*Primary Examiner* — Maury A Audet
(74) *Attorney, Agent, or Firm* — Novick, Kim & Lee, PLLC; Jae Youn Kim

(57) ABSTRACT

The present invention relates to a peptide for preventing or treating inflammatory diseases and a use thereof. According to the novel dimeric or trimeric peptide according to the present invention, it is possible to not only exhibit an excellent therapeutic effect through anti-inflammatory action but also have a very small-sized peptide, thereby minimizing side effects due to the administration of external substances. Therefore, it is expected that the peptide can be used as an active substance that can replace existing therapeutic agents for inflammatory diseases.

8 Claims, 9 Drawing Sheets

Specification includes a Sequence Listing.

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: PSP dimer

<400> SEQUENCE: 1

Pro Ser Pro Pro Ser Pro
1               5

<210> SEQ ID NO 2
<211> LENGTH: 9
<212> TYPE: PRT
<213> ORGANISM: Artificial Sequence
<220> FEATURE:
<223> OTHER INFORMATION: PSP trimer

```
<400> SEQUENCE: 2

Pro Ser Pro Pro Ser Pro Pro Ser Pro
1               5
```

PEPTIDE FOR PREVENTING OR TREATING INFLAMMATORY DISEASES AND USE THEREOF

TECHNICAL FIELD

The present invention relates to a peptide for preventing or treating inflammatory diseases and a use thereof.

The present invention is achieved by the project number of KDDF201404-04 under the support of the governmental department in Korea, the research management organization of the project is the Korea Drug Development Fund, the name of the research business is the government-funded virtual oncology drug development, the name of the research project is the deduction of arthritis-improving leading substance using cytokine-derived peptide SIS-1, and the research period is from Jul. 1, 2014 to Jun. 30, 2016.

This application claims priority to and the benefit of Korean Patent Application Nos. 10-2016-0028227 and 10-2016-0134176 filed in the Korean Intellectual Property Office on Mar. 9, 2016 and Oct. 17, 2016, the entire contents of which are incorporated herein by reference.

BACKGROUND ART

Inflammation is a phenomenon that occurs for a series of defenses purposes of minimizing the response and restoring the damaged part to n original state when cells or tissues are damaged by some cause, and causes nerves and blood vessels, lymphatic vessels, body fluids, and cellular reactions, resulting in pain, swelling, redness, fever, etc., to cause dysfunction. The causes of the inflammation include physical factors caused by trauma, frostbite, burn, radioactivity, chemical factors caused by chemicals such as acid, and immunological factors due to antibody response, and in addition, caused by blood vessel or hormone imbalance. Cells damaged by external stimuli secrete a variety of biological mediators such as pro-inflammatory cytokines and chemokines, interleukins, and interferons, resulting in vasodilation and antibodies, complement, plasma, and phagocyte cells are driven into the inflammation sites as the permeability is increased. This phenomenon causes erythema. A drug that acts to remove an inflammatory source to eliminate the inflammation and to reduce vital reaction and symptoms is called an anti-inflammatory agent. Until now, substances used for the purpose of anti-inflammation include ibuprofen, indomethacin, and the like as non-steroids and dexamethasone and like as steroids, but the use thereof is limited because of the safety problem thereof. In this respect, development of safe anti-inflammatory agents with maximum efficacy and minimal side effects is required.

Arthritis, a typical inflammatory disease, is one of the most painful diseases suffered by humans and causes major disabilities in daily life due to walking disorders as well as pain.

The arthritis is classified into bacterial arthritis caused by bacteria and aseptic arthritis irrelevant to the bacteria and is known to be more than 100 kinds of arthritis.

The most common arthritis includes degenerative arthritis, rheumatoid arthritis, gouty arthritis, lupus, and gout. It is searched that 47 of 1,000 people in Korea suffer from arthritis, and it is shown that a total of 1.9 million people suffer from arthritis all over the nation. Arthritis, as a leading cause of long-term disability, is pointed out as the biggest cause of disability in the elderly over the age of 65 in the United States.

Even in Korea, arthritis is shown as a major disease of long-term disability following stroke, and it is known that women are more likely to suffer from arthritis than men.

For the treatment of arthritis, rheumatoid arthritis may be treated with drug therapy such as anti-inflammatory analgesic drugs, steroids, gold therapy, local injection of steroids, and immunosuppressive therapy, surgical therapy, and appropriate physical exercise therapy within the limits of not moving the joint too much, as well as general conservative treatments such as feeding of food and nutrients and fixing and splint. On the other hand, in the case of degenerative arthritis, appropriate exercise and rehabilitation treatment, drug therapy of administering anti-inflammatory analgesic agents, adrenocortical hormones, cartilage protecting agents, intra-articular lubricants and the like, or surgical therapy may be performed.

Drugs used in the treatment of arthritis are used to reduce pain and edema and slow the progression of the disease. However, these arthritis therapeutic agents have gastrointestinal disorders as side effects and gastric ulcers and hemorrhages when taken for a long time.

The causes for increased incidence of gastrointestinal side effects include old age over 65 years, ulceration, history of bleeding, combination of steroids or anticoagulants, and smoking or drinking. To reduce these side effects, the condition of the body after taking the medicines is observed, taking the medication immediately is stopped at any signs of gastrointestinal side effects, the treatment needs to be discussed with your doctor, and the drug needs to be changed to medicines with low gastrointestinal side effects (selective anti-inflammatory drugs, COX-2 inhibitors). The arthritis therapeutic agents used in a current clinical practice are mainly low-molecular drugs as disease-modifying antirheumatic drugs (DMARDs) such as methotrexate (MTX) as a non-steroidal anti-inflammatory drug, hydroxychloroquine and auranofin, and protein drugs such as Etanercept (Enbrel as proprietary name), Infliximab (Remicade as proprietary name) and Adalimumab (Humira as proprietary name), which have been developed as TNF-α inhibitors. Although methotrexate is a drug which is originally developed as an anticancer drug and has been currently used as an arthritis therapeutic agent, but due to toxicity to normal cells, long-term use of methotrexate causes serious side effects, and as a result, more than 50% of patients are reported to have failed treatment.

Under such a background, development of a novel therapeutic agent having an effective therapeutic effect while minimizing side effects of conventional anti-inflammatory agents, especially arthritis therapeutic agents, has been required and has been actively studied (Korean Patent Publication No. 10-2015-0125001), but it is still not enough.

DISCLOSURE

Technical Problem

In order to solve the above problems, the present inventors prepared a dimeric or timeric peptide, confirmed an excellent anti-inflammatory effect according to administration of peptides using a mouse model of rheumatoid arthritis as a representative inflammatory disease, and completed the present invention based thereon.

An object of the present invention is to provide a peptide consisting of amino acid represented by SEQ ID NO: 1 or 2.

Another object of the present invention is to provide a pharmaceutical composition for preventing or treating an inflammatory disease, containing the peptide or a polynucleotide encoding the peptide as an active ingredient.

Yet another object of the present invention is to provide a health functional food/cosmetic composition for preventing or improving an inflammatory disease, containing the peptide as an active ingredient.

However, technical objects of the present invention are not limited to the aforementioned purpose and other objects which are not mentioned may be clearly understood to those skilled in the art from the following description.

Technical Solution

In order to achieve the object, in one aspect, the present invention provides a peptide consisting of amino acid represented by SEQ ID NO: 1 or 2.

In a preferred embodiment, an N- or C-terminal of the peptide may bind to a protective group which is selected from the group consisting of an acetyl group, a fluorenylmethoxy carbonyl group, a formyl group, a palmitoyl group, a myristyl group, a stearyl group or a polyethylene glycol (PEG) group.

In another aspect, the present invention provides a pharmaceutical composition for preventing or treating an inflammatory disease, containing a peptide consisting of amino acid represented by SEQ ID NO: 1 or 2 or a polynucleotide encoding the peptide as an active ingredient.

In a preferred embodiment, the inflammatory disease may be selected from the group consisting of atopic, psoriasis, dermatitis, allergies, arthritis, rhinitis, otitis media, sore throat, tonsillitis, cystitis, nephritis, pelvic inflammatory disease, Crohn's disease, ulcerative colitis, ankylosing spondylitis, systemic lupus erythematodes (SLE), asthma, edema, delayed allergy (IV type allergy), graft rejection, graft versus host disease, autoimmune encephalopathy, multiple sclerosis, inflammatory bowel disease, cystic fibrosis, diabetic retinopathy, ischemia-reperfusion injury, vascular restenosis, glomerulonephritis, and gastrointestinal allergy.

In another preferred embodiment, the composition may inhibit generation of inflammatory cytokine.

In still another preferred embodiment, the composition may further include a pharmaceutically acceptable carrier.

In yet another preferred embodiment, the composition may be simultaneously, separately or sequentially administered with other anti-inflammatory agents in addition to the peptide consisting of amino acid represented by SEQ ID NO: 1 or 2 or the polynucleotide encoding the peptide.

In still yet another preferred embodiment, the composition may be formulated for oral administration, intramuscular administration, intravenous administration, intraperitoneal administration, subcutaneous administration, intradermal administration, or topical administration.

In yet another aspect, the present invention provides a health functional food/cosmetic composition for preventing or improving an inflammatory disease, containing the peptide as an active ingredient.

In still another aspect, the present invention provides a method for treating an inflammatory disease including administering the peptide to a subject.

In still yet another aspect, the present invention provides a use for treating an inflammatory disease of the peptide.

Advantageous Effects

According to the novel dimeric or trimeric peptide according to the present invention, it is possible to not only exhibit an excellent therapeutic effect through anti-inflammatory action but also have a very small-sized peptide, thereby minimizing side effects due to the administration of external substances and will be expected to be used as an active substance that can replace existing therapeutic agents for inflammatory diseases.

MODES OF THE INVENTION

Figure 1:
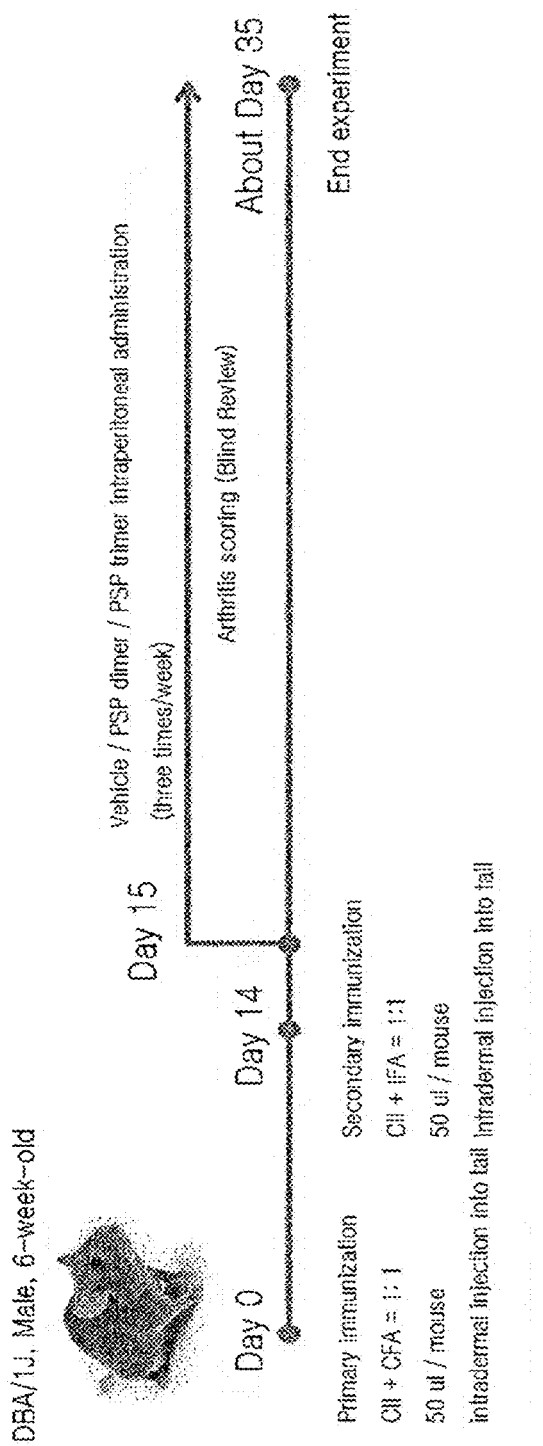
FIG. 1 is a schematic diagram schematically illustrating a preparation process of a collagen-induced arthritis mouse model and an administration timing of a peptide (a PSP dimer or a PSP trimer) of the present invention.

Hereinafter, the present invention will be described in detail.

The present invention provides a peptide consisting of amino acid represented by SEQ ID NO: 1 or 2.

In the present invention, the "peptide" refers to a polymer consisting of two or more amino acids linked by an amide bond (or a peptide bond) and refers to a peptide having anti-inflammatory activity for the purpose of the present invention. Despite various studies on a peptide therapeutic agent, there is a disadvantage that the peptide is too large in self-size to effectively introduce target tissues or cells, or has a short half-life and disappears in the body in a short period. As a result, the present invention has a technical meaning in that a dimeric or trimeric peptide consisting of 10 amino acids or less while having an effective anti-inflammatory activity is first established.

The peptide of the present invention may consist of amino acid represented by SEQ ID NO: 1 or 2, and may include an amino acid sequence having sequence homology with the amino acid sequence represented by SEQ ID NO: 1 or 2 of 75% or more, preferably 80% or more, more preferably 90% or more and most preferably 95% or more, and may additionally include an amino acid sequence prepared for the specific purpose of increasing a targeting sequence, a tag, a labeled residue, half-life, or peptide stability.

In addition, the peptide of the present invention may be obtained by various methods well known in the art. For example, the peptide may be prepared by polynucleotide recombination and protein expression systems or synthesis in vitro through chemical synthesis such as peptide synthesis, and cell-free protein synthesis.

In addition, to obtain better chemical stability, enhanced pharmacological properties (half-life, absorbency, potency, efficacy, etc.), altered specificity (e.g., broad biological activity spectrum), and reduced antigenicity, a protective group may bind to an N- or C-terminal of the peptide. Preferably, the protective group may be an acetyl group, a fluorenylmethoxycarbonyl group, a formyl group, a palmitoyl group, a myristyl group, a stearyl group or a polyethylene glycol (PEG) group, but may include any ingredient capable of enhancing modification of the peptide, particularly, stability of the peptide, without limitation. The term "stability" used in the present invention refers to storage stability (for example, room-temperature storage stability) as well as in-vivo stability that protects the peptide of the present invention from attack of a protein cleavage enzyme in vivo.

In the present invention, "polynucleotide" is a polymer to which a nucleotide binds, and serves to transmit genetic information. For the purpose of the present invention, the polynucleotide encodes the peptide of SEQ ID NO: 1 or 2 and may include a polynucleotide sequence encoding the peptide and a sequence having sequence homology of 75% or more, preferably 85% or more, more preferably 90% or more, and most preferably 95% or more.

The term "homology" used in the present invention is to indicate a similar degree to a wide-type amino acid sequence or a polynucleotide sequence, and the comparison of the homology may be performed using a comparison program which is well-known in the art and homology between at least two sequences may be calculated by a percentage (%).

In another aspect of the present invention, the present invention provides a pharmaceutical composition for preventing or treating an inflammatory disease, containing the peptide or a polynucleotide encoding the peptide as an active ingredient; a use of a peptide consisting of amino acid represented by SEQ ID NO: 1 or 2 for treating an inflammatory disease; and a method for treating an inflammatory disease including administering a therapeutically effective dose of peptide to a subject.

The term "prevention" used in the present invention means all actions for inhibiting the inflammatory disease or delaying the onset by administering the pharmaceutical composition according to the present invention.

The term "treatment" used in the present invention means all actions for improving or beneficially changing symptoms for the inflammatory disease by administering the pharmaceutical composition according to the present invention.

In the present invention, the "subject" refers to a subject requiring treatment of an inflammatory disease, and more specifically, refers to human or non-human primates, and mammals such as mouse, dogs, cats, horses, and cows.

The "inflammatory disease" which is a disease to be prevented or treated by the composition of the present invention refers to a generic term of a disease having inflammation as a lesion and is not limited thereto. Preferably, the inflammatory disease may be atopic, psoriasis, dermatitis, allergies, arthritis, rhinitis, otitis media, sore throat, tonsillitis, cystitis, nephritis, pelvic inflammatory disease, Crohn's disease, ulcerative colitis, ankylosing spondylitis, systemic lupus erythematodes (SLE), asthma, edema, delayed allergy (IV type allergy), graft rejection, graft versus host disease, autoimmune encephalopathy, multiple sclerosis, inflammatory bowel disease, cystic fibrosis, diabetic retinopathy, ischemia-reperfusion injury, vascular restenosis, glomerulonephritis, or gastrointestinal allergy. Herein, arthritis refers to a disease caused by a inflammatory change in the joints due to various causes such as bacteria, trauma, autoimmune diseases, and the like, and may be preferably osteoarthritis, degenerative arthritis, rheumatoid arthritis, osteochondritis dissecans, joint ligament injury, medial meniscus injury, malalignment of joints, avascular necrosis, and juvenile idiopathic arthritis and most preferably rheumatoid arthritis.

According to an embodiment of the present invention, a dimeric or trimeric peptides was prepared using PSP monomers (see Example 1), a decrease in arthritis progression index was confirmed using a mouse model of rheumatoid arthritis, a typical inflammatory disease, and inhibition of immune cell infiltration and pannus formation at the injured joint site, reduction of the expression level of IL-18, and a therapeutic effect according to an anti-inflammatory activity of the peptide in comparison with methotrexate as a conventional arthritis therapeutic agent were confirmed (see Example 2).

The term "anti-inflammatory activity" used in the present invention refers to inhibition of the inflammatory response, and the inflammation, which is one of defensive responses of biological tissues to any stimuli, refers to a complicated lesion which is developed together with tissue degeneration, circulatory disturbance and exudation, and tissue proliferation.

The pharmaceutical composition of the present invention which is one of these anti-inflammatory activities, may inhibit inflammatory cytokines, and the inflammatory cytokine may be preferably interleukin-18 (IL-18), but is not limited thereto.

Meanwhile, the peptide or the polynucleotide encoding the peptide of the present invention may be delivered to a pharmaceutically acceptable carrier such as a colloidal suspension, powder, saline, lipid, liposome, microspheres, or nanospheric particles. The peptide or the polynucleotide may form a complex with a carrier or associated with the carrier and may be delivered in vivo using a delivery system which is known in the art, such as lipids, liposomes, microparticles, gold, nanoparticles, polymers, condensation reagents, polysaccharides, polyamino acids, dendrimers, saponins, adsorption enhancers or fatty acids.

In addition, the pharmaceutically acceptable carrier includes lactose, dextrose, sucrose, sorbitol, mannitol, starch, acacia, rubber, calcium phosphate, alginate, gelatin, calcium silicate, microcrystalline cellulose, polyvinylpyrrolidone, cellulose, water, syrup, methylcellulose, hydroxybenzoate, propylhydroxybenzoate, talc, magnesium stearate, mineral oil, and the like, which are generally used in formulation, but is not limited thereto. Further, the pharmaceutical composition may further include lubricants, wetting agents, sweeteners, flavors, emulsifiers, suspensions, preservatives, and the like in addition to the ingredients.

The pharmaceutical composition of the present invention may be administered orally or parenterally (for example, intramuscularly, intravenously, intraperitoneally, subcutaneously, intradermally, or topically) depending on the intended method, and the dose varies according to the condition and weight of a patient, the degree of disease, a type of drug, and the route and time of administration, but may be suitably selected by those skilled in the art.

The pharmaceutical composition of the present invention is administered with a pharmaceutically effective dose, for example, 0.1 to 10 µmol. In the present invention, the "pharmaceutically effective dose" refers to a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a route of administration, and an emission rate, duration of treatment, and simultaneously used drugs and other elements well-known in the medical field.

The pharmaceutical composition according to the present invention may be administered as an individual therapeutic agent or in combination with other anti-inflammatory agents, simultaneously, separately or sequentially administered with existing anti-inflammatory agents, and administered singly or multiply. It is important to administer an amount capable of obtaining a maximum effect with a minimal amount without side effects by considering all of the elements and the amount may be easily determined by those skilled in the art.

In particular, the effective dose of the pharmaceutical composition according to the present invention may vary according to age, gender, condition, and weight of the patient, absorption of active ingredients in the body, inactive rate, excretion rate, disease type, and combined drugs, and may be increased or decreased according to the route of administration, the severity of obesity, gender, weight, age, and the like.

Further, in another aspect of the present invention, the present invention provides a health functional food/cosmetic composition for preventing or improving an inflammatory disease, containing the peptide as an active ingredient.

The term "improvement" used in the present invention means all actions that at least reduce parameters associated with a treated condition, for example, the degree of symptoms. At this time, the health functional food composition may be used simultaneously or separately with the drug for treatment before or after the onset of the corresponding disease for preventing or improving the inflammatory disease.

In the health functional food composition of the present invention, the active ingredient may be added to the food as it is or may be used together with other food or food ingredients, and may be appropriately used according to general methods. A mixing amount of the active ingredients may be appropriately determined according to a purpose of use (for prevention or improvement) thereof. Generally, in preparation of foods or beverages, the composition of the present invention may be added with an amount of preferably 15 wt % or less and more preferably 10 wt % or less with respect to a raw material. However, in the case of long-term ingestion for the purpose of health and hygiene or health regulation, the amount may be below the above range.

The health functional food composition of the present invention may contain other ingredients as a required ingredient without specific limitation other than the active ingredient. For example, like a general beverage, various flavoring agents or natural carbohydrates may be added as an additional ingredient. Examples of the aforementioned natural carbohydrates include general sugars, such as monosaccharides, for example, glucose, fructose, and the like; disaccharides, for example, maltose, sucrose, and the like; and polysaccharides, for example, dextrin, cyclodextrin, and the like, and sugar alcohols, such as xylitol, sorbitol, and erythritol. As the flavoring agents other than the above examples, natural flavoring agents (thaumatin and *stevia* extract (e.g., rebaudioside A, glycyrrhizin, etc.) and synthetic flavoring agents (saccharin, aspartame, etc.) may be advantageously used. The ratio of the natural carbohydrate may be appropriately determined by selection of those skilled in the art.

In addition, the health food composition according to the present invention may contain various nutrients, vitamins, minerals (electrolytes), flavoring agents such as synthetic flavoring agents and natural flavoring agents, coloring agents and thickening agents (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of such additives may also be appropriately selected by those skilled in the art.

The cosmetic composition of the present invention may be prepared by any formulation which is generally prepared in the art and for example, may be formulated by a solution, a suspension, an emulsion, paste, gel, cream, lotion, powder, soap, a surfactant-containing cleanser, oil, powder foundation, emulsion foundation, wax foundation, spray and the like, but is not limited thereto. More particularly, the cosmetic composition of the present invention may be prepared by a formulation of emulsion lotion, nutrition lotion, nourishing cream, massage cream, essence, eye cream, cleansing cream, cleansing foam, cleansing water, pack, spray or powder.

The effective carrier contained in the cosmetic composition of the present invention may use a carrier which is generally used in the art depending on the formulation. When the formulation of the present invention is paste, cream, or gel, as a carrier ingredient, animal oil, vegetable oil, waxes, paraffins, starch, tragacanth, cellulose derivatives, polyethylene glycol, silicone, bentonite, silica, talc, zinc oxide, or the like may be used.

When the formulation of the present invention is the powder or the spray, as the carrier ingredient, lactose, talc, silica, aluminum hydroxide, calcium silicate, or polyamide powder may be used. Particularly, in the case of the spray, a propellant such as chlorofluoro hydrocarbon, propane/butane or dimethyl ether may be additionally included.

When the formulation of the present invention is the solution or the emulsion, as the carrier ingredient, a solvent, a dissolving agent, or an emulsifying agent is used, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or sorbitan fatty acid ester is included.

When the formulation of the present invention is the suspension, as the carrier ingredient, a liquid diluent such as water, ethanol, or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agarose or tragacanth may be used.

When the formulation of the present invention is the surfactant-containing cleanser, as the carrier ingredient, aliphatic alcohol sulfate, aliphatic alcohol ether sulfate, sulfosuccinate monoester, isethionate, imidazolinium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, or the like may be used.

The ingredients contained in the cosmetic composition of the present invention may contain ingredients which are generally used in the cosmetic composition in addition to the active ingredients and the carrier ingredients, and for example, may contain general adjuvants such as antioxidants, stabilizers, solubilizers, vitamins, pigments and fragrances.

Hereinafter, preferred Examples for helping in understanding of the present invention are proposed. However, the following Examples are provided for more easily understanding the present invention and the contents of the present invention are not limited by the following Examples.

EXAMPLES

Example 1

Preparation of Peptide

In Example 1, as illustrated in Table 1 below, a dimeric or trimeric polymer was prepared using PSP monomers. Thereafter, the synthesized peptide was purified using a high-performance liquid chromatography (SHIMADZU Prominence HPLC) and a column used a Shiseido capcell pak C18 column (4.6×50 mm). Further, the mass of the synthesized peptide was confirmed using a mass spectrometer (HP 1100 series LC/MSD).

TABLE 1

| Name of peptide | Amino acid sequence |
|---|---|
| PSP dimer | PSPPSP (SEQ ID NO: 1) |
| PSP trimer | PSPPSPPSP (SEQ ID NO: 2) |

Example 2

Analysis of Arthritis Therapeutic Effect Using Collagen-induced Arthritis Mouse Model In Example 2, using a collagen-induced arthritis mouse model in the following document, a therapeutic effect of a PSP dimer or trimer for a representative inflammatory disease, rheumatoid arthritis was confirmed (Nat Protoc. 2007; 2(5):1269-75.).

2-1. Preparation of Collagen-induced Arthritis Mouse Model and Administration of Peptide A collagen-induced arthritis (CIA) mouse model was prepared as follows, as an autoimmune disease-based arthritis model with characteristics similar to human rheumatoid arthritis.

First, a bovine type II collagen (Chondrex Corporation, USA) and a Freund's complete adjuvant (Chondrex Corporation, USA) were mixed at a ratio of 1:1 and emulsified, and then 50 μl of the emulsified collagen solution was injected intradermally into the tail of a 6-week-old DBA/1J mouse to induce primary immunization. At two weeks after the primary immunization, the bovine type II collagen and the Freund's complete adjuvant were mixed at a ratio of 1:1 and emulsified, and then 50 μl of the emulsified collagen solution was injected intradermally into the tail of the mouse again to induce secondary immunization (boosting). After the secondary immunization, the peptide of the present invention (the PSP dimer (1 μmole) or the PSP trimer (1 μmole)) was administered intraperitoneally three times a week from the next day, and as a comparative experimental group, a PSP monomer-treated group and as a control (Vehicle control), a PBS-treated group were used, respectively. The preparation process of the collagen-induced arthritis mouse model and the administration time of the peptide were schematically illustrated in FIG. 1.

2-2. Evaluation of Deepening Degree of Arthritis

In order to investigate the development of arthritis progression according to the peptide treatment of the present invention, the deepening degree of arthritis with time was measured by evaluating an arthritis progression index. Two observers who were unaware of the specific experimental conditions evaluated progression of arthritis three times a week. In this case, the arthritis progression index was evaluated by 0 to 4 scores per leg according to an arthritis progression evaluation standard by Rossoliniec and the like in Table 2 below to be represented by a total of 0 to 16 scores (a sum of four legs), and thereafter, two observers calculated an average value of the evaluated results to digitize the severity of arthritis.

TABLE 2

| Score | symptoms |
|---|---|
| 0 | There is no edema or swelling. |
| 1 | Slight edema and redness limited to foot or ankle joint are observed. |
| 2 | Slight edema and redness from the ankle joint to the tarsal bone are observed. |
| 3 | Moderate edema and redness from the ankle joint to the tarsal bone are observed. |
| 4 | Edema and redness from the ankle to the entire leg are present and joint stiffness is observed. |

Figure 2:
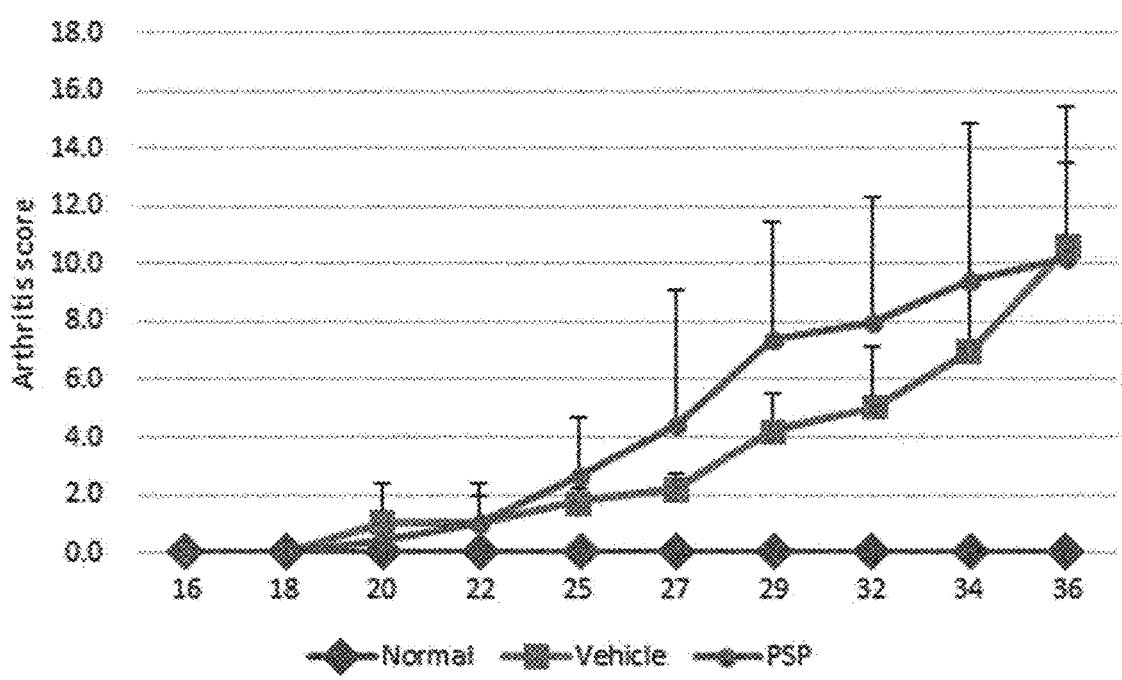
FIG. 2 illustrates a result of periodically evaluating an arthritic progression index according to peptide treatment after induction of a second immunity response in the collagen-induced arthritis mouse model (Normal: normal mouse, Vehicle control: control mouse, and PSP: PSP monomer-treated mouse).

As a result, as illustrated in Table 3 below and FIG. 2, in a control (Vehicle control) (PBS), it could be seen that on 36 day, the arthritis progressed rapidly so that the arthritis progression index reached 10.5. In addition, it could be seen that despite the treatment of the PSP monomer, the progression of arthritis was not inhibited or delayed (36th day: 10.2).

TABLE 3

|  | 16 | 18 | 20 | 22 | 25 | 27 | 29 | 32 | 34 | 36 (day) |
|---|---|---|---|---|---|---|---|---|---|---|
| Normal | 0.0 | 0.0 | 0.0 | 0.0 | 0.0 | 0.0 | 0.0 | 0.0 | 0.0 | 0.0 |
| Vehicle control | 0.0 | 0.0 | 1.0 | 1.0 | 1.8 | 2.3 | 4.3 | 5.0 | 7.0 | 10.5 |
| PSP monomer | 0.0 | 0.0 | 0.4 | 1.0 | 2.6 | 4.4 | 7.4 | 8.0 | 9.4 | 10.2 |

Figure 3:
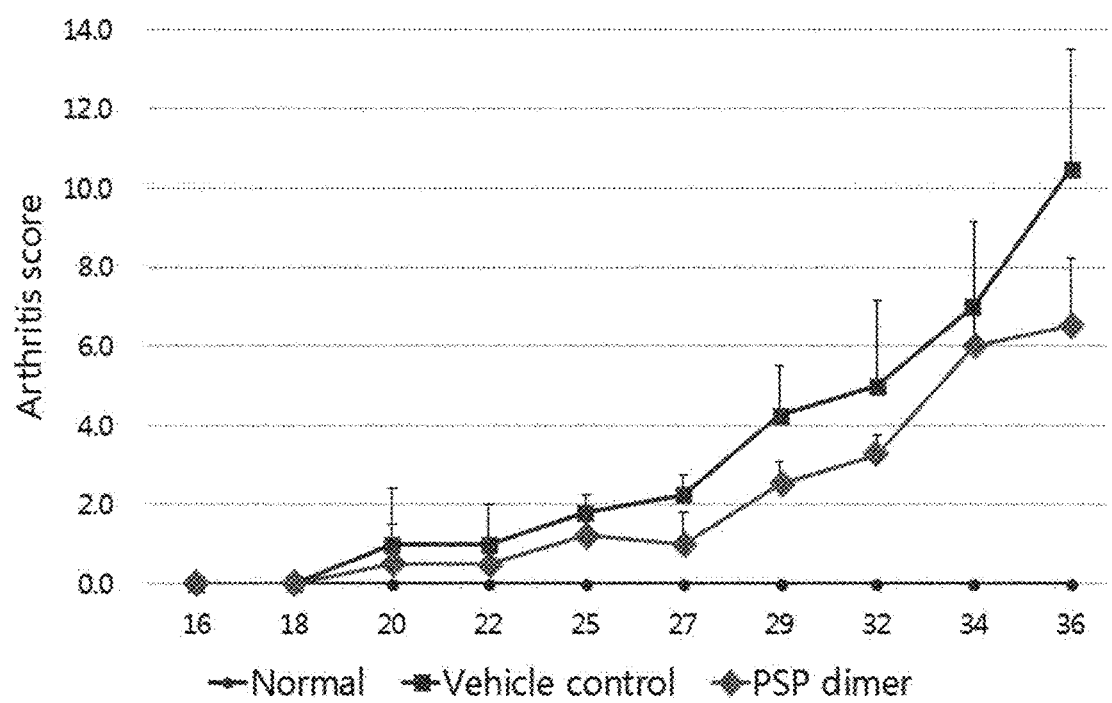
FIG. 3 illustrates a result of periodically evaluating an arthritic progression index according to peptide treatment after induction of a second immunity response in the collagen-induced arthritis mouse model (Normal: normal mouse, Vehicle control: control mouse, and PSP dimer: PSP dimer-treated mouse).
Figure 4:
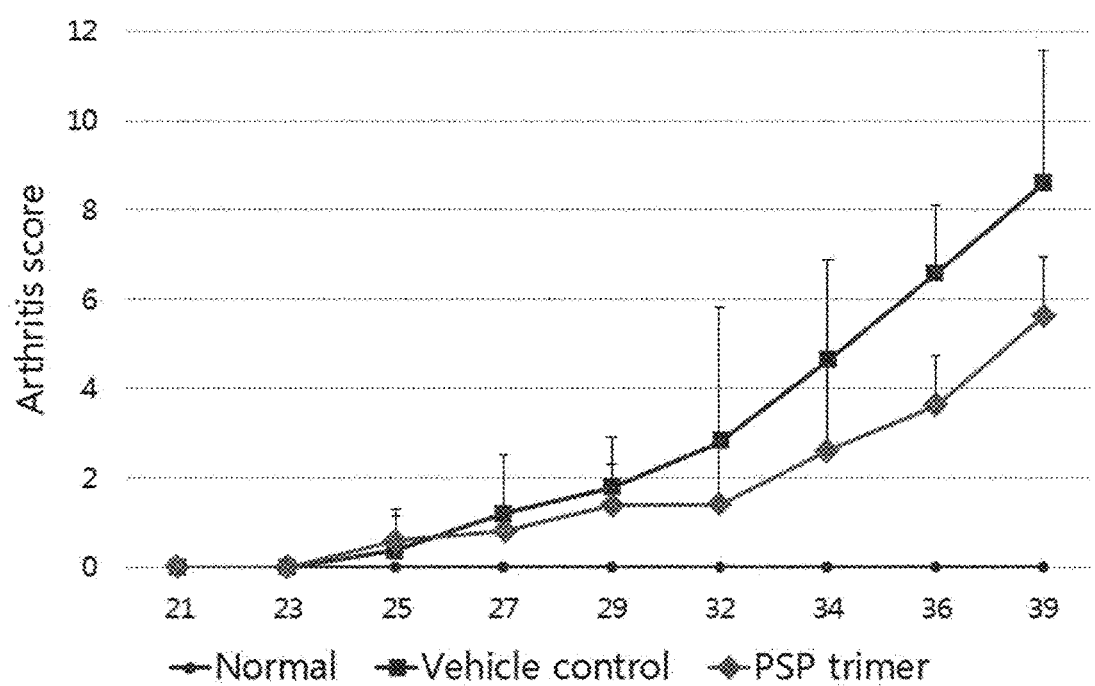
FIG. 4 illustrates a result of periodically evaluating an arthritic progression index according to peptide treatment after induction of a second immunity response in the collagen-induced arthritis mouse model (Normal: normal mouse, Vehicle control: control mouse, and PSP trimer: PSP trimer-treated mouse).
Figure 5:
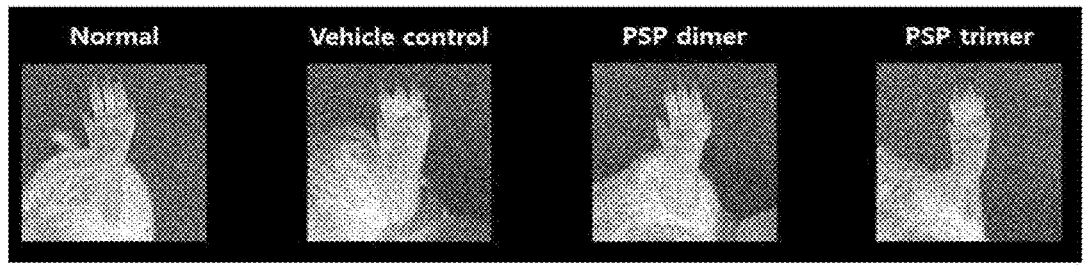
FIG. 5 illustrates a result of visually observing a mitigating effect of edema and redness around the ankle joint according to the peptide treatment of the present invention.

On the other hand, in the case of the group treated with the PSP dimer or PSP trimer, as illustrated in Tables 4 and 5 below and FIGS. 3 and 4, it could be seen that the arthritis progression index which has significantly increased in the control or the PSP monomer-treated mouse is significantly decreased as 6.5 and 5.6, respectively. Further, as the result of visually checking the degree of swelling and redness around the ankle joint, as illustrated in FIG. 5, it could be seen that the swelling and redness symptoms were remarkably mitigated in the group treated with the PSP dimer or PSP trimer as compared with the control, and as a result, significant anti-inflammatory effect and arthritis therapeutic effect were confirmed.

TABLE 4

|  | 16 | 18 | 20 | 22 | 25 | 27 | 29 | 32 | 34 | 36 (day) |
|---|---|---|---|---|---|---|---|---|---|---|
| Normal | 0.0 | 0.0 | 0.0 | 0.0 | 0.0 | 0.0 | 0.0 | 0.0 | 0.0 | 0.0 |
| Vehicle control | 0.0 | 0.0 | 1.0 | 1.0 | 1.8 | 2.3 | 4.3 | 5.0 | 7.0 | 10.5 |
| PSP dimer | 0.0 | 0.0 | 0.5 | 0.5 | 1.3 | 1.0 | 2.5 | 3.3 | 6.0 | 8.5 |

TABLE 5

|  | 21 | 23 | 25 | 27 | 29 | 32 | 34 | 36 | 39 (day) |
|---|---|---|---|---|---|---|---|---|---|
| Normal | 0.0 | 0.0 | 0.0 | 0.0 | 0.0 | 0.0 | 0.0 | 0.0 | 0.0 |
| Vehicle control | 0.0 | 0.0 | 0.4 | 1.2 | 1.8 | 2.8 | 4.6 | 8.6 | 8.6 |
| PSP trimer | 0.0 | 0.0 | 0.6 | 0.8 | 1.4 | 1.4 | 2.6 | 3.8 | 5.6 |

2-3. Histological Analysis

In order to confirm a healing effect of the cartilage damage of the joint region according to the peptide treatment of the present invention, the deepening degree of arthritis in Example 2-2 was evaluated and then, a histological analysis was performed. Particularly, the hind leg joint tissue of the mouse was collected and fixed with 10% formalin. Thereafter, after the calcite was removed from the bone, paraffin fragments of the tissue were prepared and lesion sites were observed through Hematoxylin & Eosin (H&E) staining.

Figure 6:
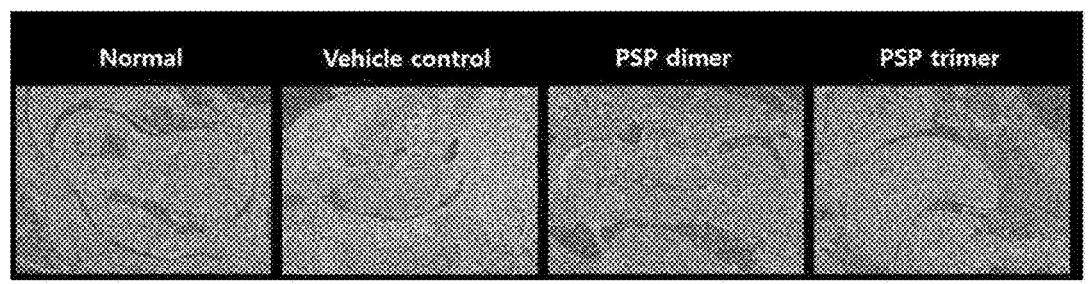
FIG. 6 illustrates a result of confirming a healing effect of the cartilage damage in the joint region according to the peptide treatment of the present invention through histological examination.

As a result, as illustrated in FIG. 6, as compared with a normal mouse (Normal), in a control mouse (Vehicle control, PBS), immune cell infiltration, pannus formation, cartilage destruction, and bone erosion of the joint region were observed as the major histopathologic opinion of arthritis progression. On the contrary, in the group treated with the PSP dimer and the PSP trimer, it could be seen that the characteristic phenomenon described above was greatly reduced and the joint region was recovered to be close to the normal mouse.

2-4. Analysis of Inflammatory Cytokine

Rheumatoid arthritis is one of chronic inflammatory diseases and it has been reported to increase the concentration of inflammatory cytokine such as interleukin-18 (IL-18) even in the joint tissues as well as the blood of a patient with rheumatoid arthritis. Based on these facts, in Example 2, the arthritis therapeutic effect according to the peptide treatment of the present invention was confirmed through a change in expression level of IL-18. The expression of IL-18 was measured by using immunohistochemistry (IHC), and to this end, a paraffin ingredient was removed from the paraffin tissue fragment and then rehydrated to create an environment in which the antibodies may be stained. Thereafter, an anti-IL-18 antibody was treated, each tissue section was stained, and the antibody binding to IL-18 was reddish using a DAB substrate.

Figure 7:
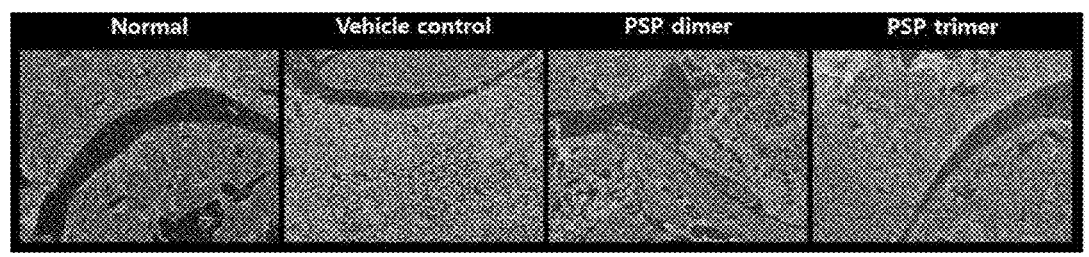
FIG. 7 illustrates a result of confirming the reduction of an expression level of IL-18 in the joint region according to the peptide treatment of the present invention through immunohistochemistry (IHC).

As a result, as illustrated in FIG. 7, as compared with a normal mouse (Normal), in the control mouse (Vehicle control, PBS), as reported in the related art, the expression of IL-18 was significantly increased. On the contrary, in the group treated with the PSP dimer and the PSP trimer, it could be seen that the expression of IL-18 was largely decreased to the normal mouse level.

2-5. Comparison with Methotrexate in Arthritis Therapeutic Effect

Methotrexate (MTX), one of drugs which are used as arthritis therapeutic agents in a current clinical practice, had excellent anti-inflammatory and arthritis therapeutic effects as an immunodepressant, but may have side effects such as toxicity to normal cells, oral ulcer, alopecia, interstitial pneumonia, bone marrow suppression, and the like. As a result, the methotrexate is known as a drug that needs to pay close attention after medication with sufficient medication counseling. In Example 2, the arthritis therapeutic effect with the peptide of the present invention and methotrexate (1 mg/kg) was evaluated and compared with the arthritic progression index by using the same method as Example 2-2.

Figure 8:
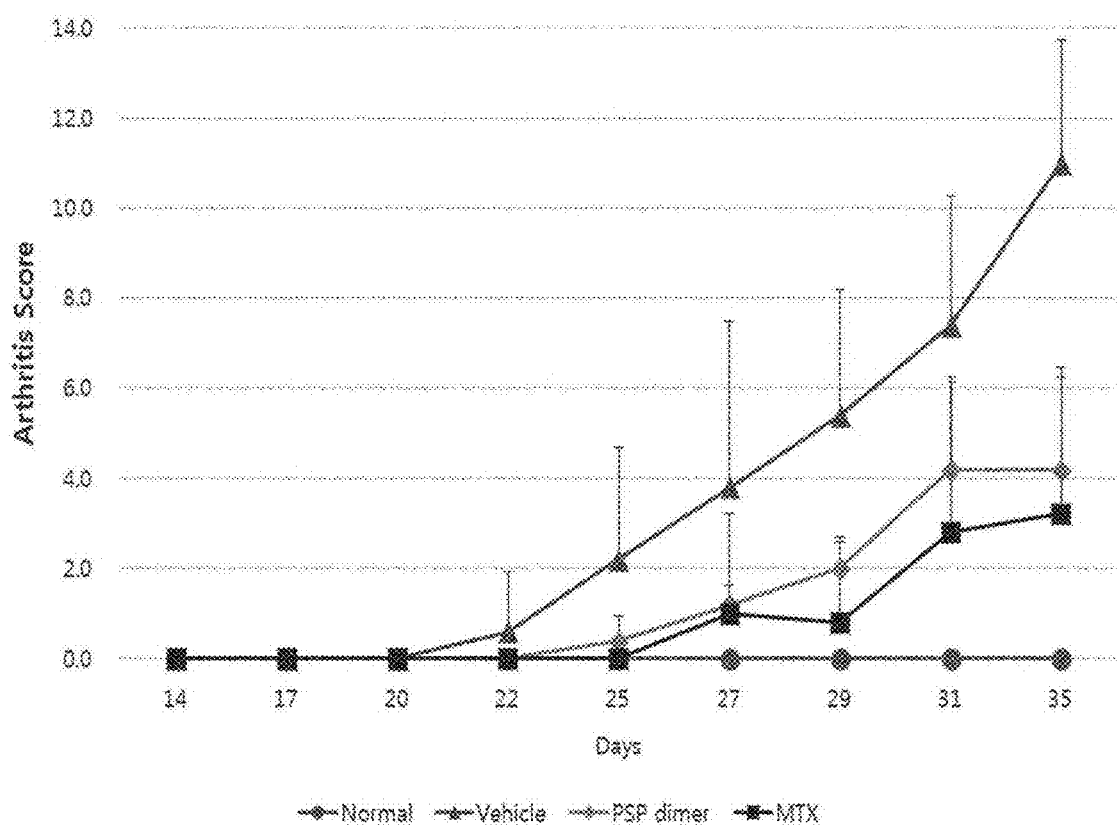
FIG. 8 illustrates a result of periodically evaluating an arthritic progression index according to treatment of a PSP dimmer and methotrexate after induction of a second immunity response in the collagen-induced arthritis mouse model (Normal: normal mouse, Vehicle: control mouse, PSP dimer: PSP dimer-treated mouse, and MTX: methotrexate-treated mouse).
Figure 9:
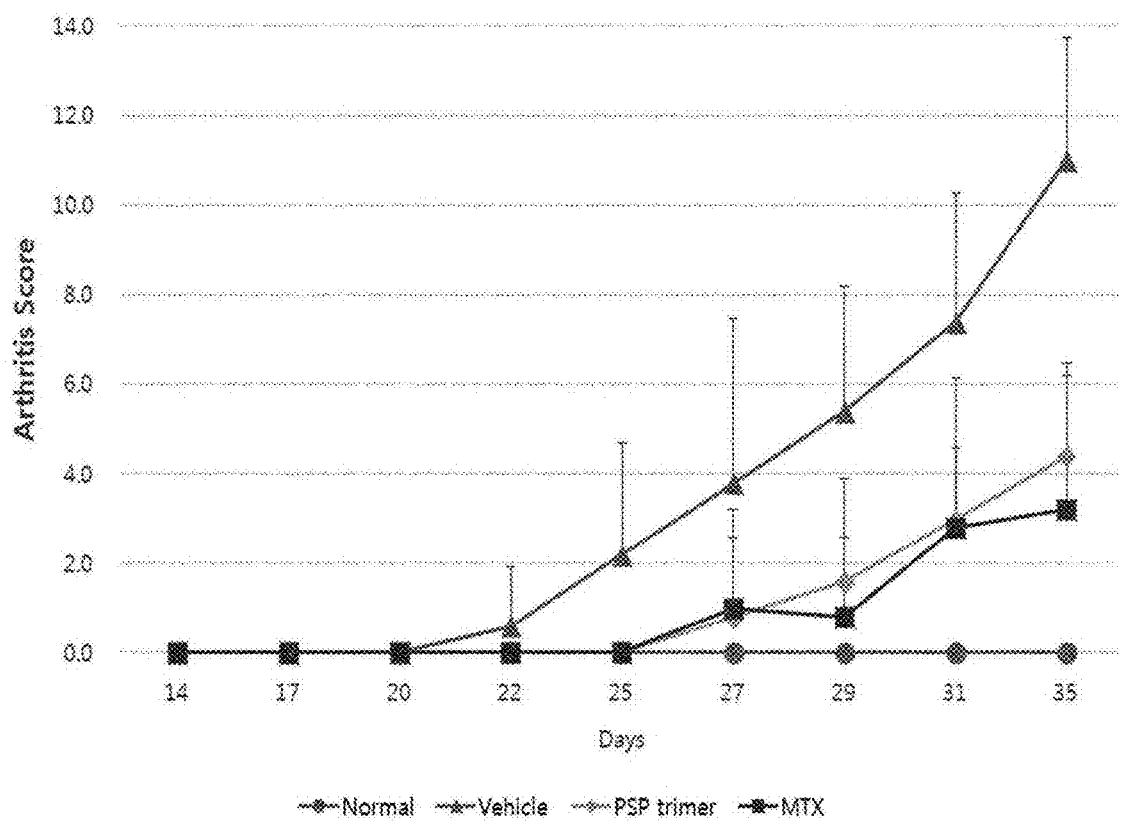
FIG. 9 illustrates a result of periodically evaluating an arthritic progression index according to treatment of a PSP trimer and methotrexate after induction of a second immunity response in the collagen-induced arthritis mouse model (Normal: normal mouse, Vehicle: control mouse, PSP trimer: PSP trimer-treated mouse, and MTX: methotrexate-treated mouse).

As a result, as illustrated in Tables 6 and 7 and FIGS. 8 and 9, all the groups treated with the PSP dimer and the PSP trimer showed an approximate arthritis progression index to the group treated with methotrexate and confirmed the excellent therapeutic effect again.

TABLE 6

|  | 14 | 17 | 20 | 22 | 25 | 27 | 29 | 31 | 35 (day) |
|---|---|---|---|---|---|---|---|---|---|
| Normal | 0.0 | 0.0 | 0.0 | 0.0 | 0.0 | 0.0 | 0.0 | 0.0 | 0.0 |
| Vehicle control | 0.0 | 0.0 | 0.0 | 0.6 | 2.2 | 3.8 | 5.4 | 7.4 | 11.0 |
| PSP dimer | 0.0 | 0.0 | 0.0 | 0.0 | 0.4 | 1.2 | 2.0 | 4.2 | 4.2 |
| MTX | 0.0 | 0.0 | 0.0 | 0.0 | 0.0 | 1.0 | 0.8 | 2.8 | 3.2 |

TABLE 7

|  | 14 | 17 | 20 | 22 | 25 | 27 | 29 | 31 | 35 (day) |
|---|---|---|---|---|---|---|---|---|---|
| Normal | 0.0 | 0.0 | 0.0 | 0.0 | 0.0 | 0.0 | 0.0 | 0.0 | 0.0 |
| Vehicle control | 0.0 | 0.0 | 0.0 | 0.6 | 2.2 | 3.8 | 5.4 | 7.4 | 11.0 |
| PSP trimer | 0.0 | 0.0 | 0.0 | 0.0 | 0.8 | 1.6 | 3.0 | 4.4 | |
| MTX | 0.0 | 0.0 | 0.0 | 0.0 | 0.0 | 1.0 | 0.8 | 2.8 | 3.2 |

When describing the results, it can be seen that the peptide (the PSP dimer or the PSP trimer) of the present invention may effectively mitigate the inflammatory response of the typical inflammatory disease, rheumatoid arthritis, and may be used as an active substance for the treatment of the inflammatory diseases.

Example 3

Evaluation of Toxicity

In Example 3, in order to confirm the toxicity of the peptide of the present invention, the PSP dimer or the PSP trimer was intraperitoneally administered to mouse at various concentrations (0.1 µmole, 1 µmole, and 10 µmole), and then the mortality and a change in body weight of each mouse were measured. On the other hand, as a control, a non-administration group (Normal) and a PBS-treated group (PBS) were used.

Figure 10:
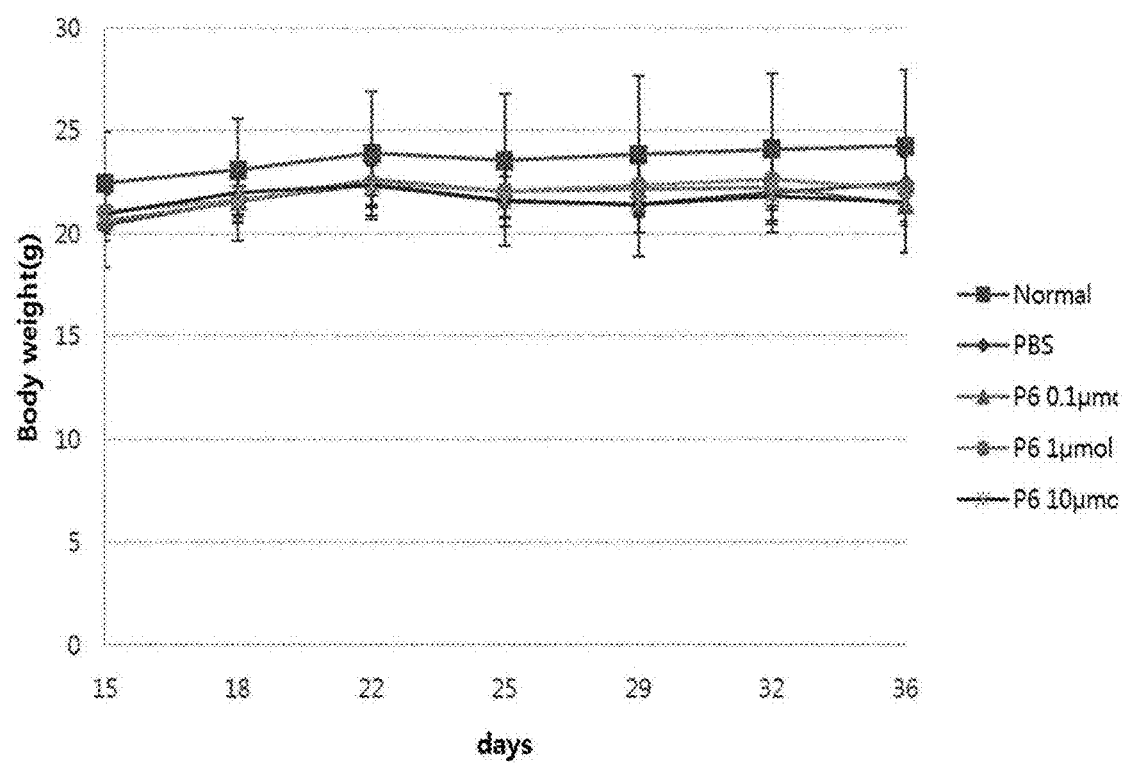
FIG. 10 illustrates a result of confirming a change in body weight after intraperitoneal administration of a PSP dimer (P6) to mouse at various concentrations (0.1 μmole, 1 μmole, and 10 μmole).
Figure 11:
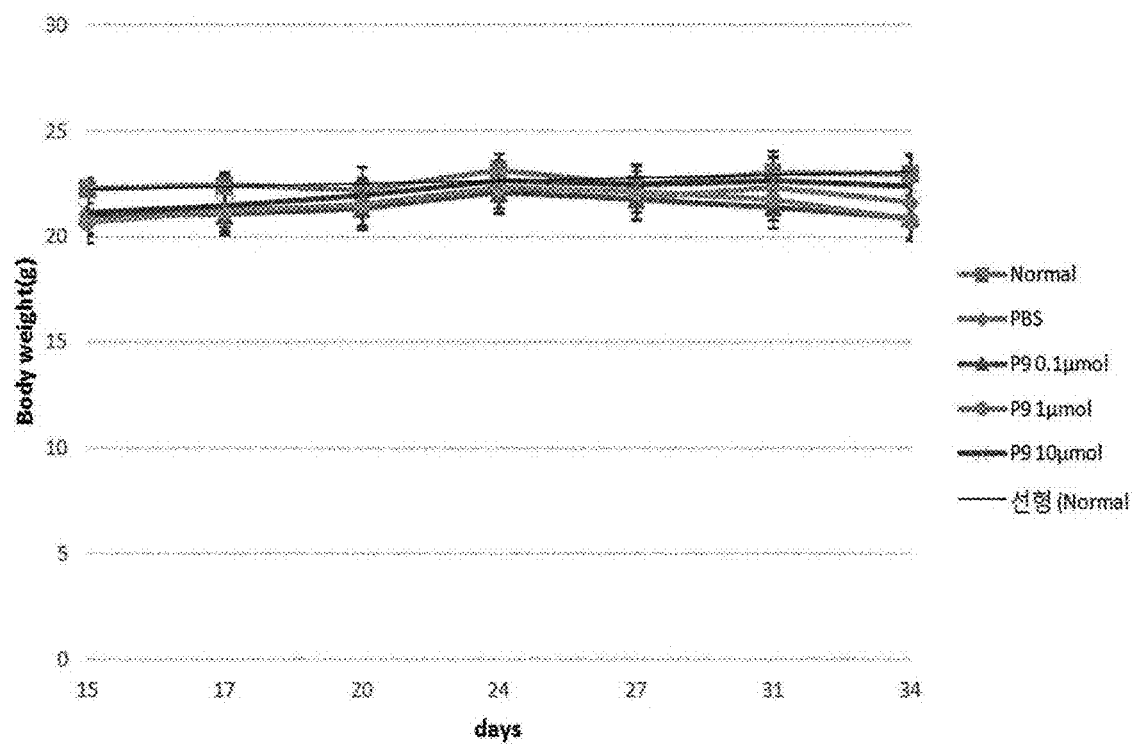
FIG. 11 illustrates a result of confirming a change in body weight after intraperitoneal administration of a PSP trimer (P9) to mouse at various concentrations (0.1 μmole, 1 μmole, and 10 μmole).

As a result, even at concentrations of 1 µmole and 10 µmole which had the excellent arthritis therapeutic effect in Example 2, the morality of the mouse according to the peptide treatment was not observed. As illustrated in Tables 8 and 9 below and FIGS. 10 and 11, at all the concentrations, the mouse did not have a large difference in body weight from that of the control, and as a result, it can be seen that the peptide of the present invention is a safe ingredient which does not cause the toxicity in vivo.

TABLE 8

Body weight (g)

| | | Days | | | | | | |
|---|---|---|---|---|---|---|---|---|
| | | 15 | 18 | 22 | 25 | 29 | 32 | 36 |
| Normal | 1 | 24 | 22.8 | 21.6 | 20.1 | 21.6 | 20.3 | 26.1 |
| | 2 | 20.7 | 24.6 | 28.1 | 21.5 | 29.3 | 29.5 | 29.7 |
| | 3 | 22.2 | 21.1 | 25.8 | 28.1 | 19.9 | 26.1 | 22.8 |
| | 4 | 19.7 | 26.5 | 23.2 | 22.7 | 26.1 | 22.3 | 20.4 |
| | 5 | 25.8 | 20.4 | 20.8 | 25.5 | 22.5 | 22.4 | 22.3 |
| PBS | 1 | 22.2 | 23.7 | 24.4 | 24.2 | 23.7 | 23.1 | 23.8 |
| | 2 | 21.2 | 22.1 | 22.1 | 21.7 | 21.3 | 21.5 | 21.5 |
| | 3 | 19.8 | 21 | 21.1 | 20 | 19.8 | 20.9 | 22 |
| | 4 | 18.4 | 20 | 21.1 | 20.2 | 20.5 | 21.7 | 21.8 |
| | 5 | 23.2 | 23.7 | 24.8 | 24.3 | 25 | 25.3 | 25.7 |
| | 6 | 17.9 | 19.1 | 21.1 | 19.3 | 18.3 | 19.7 | 19.9 |
| PSP dimer 0.1 µmol | 1 | 20.7 | 20.7 | 23.3 | 22.7 | 23.2 | 23.5 | 23.7 |
| | 2 | 20.2 | 21.1 | 21.9 | 21.4 | 21.7 | 22.1 | 18.6 |
| | 3 | 21.6 | 22.7 | 23.5 | 22.1 | 22.7 | 23.3 | 22.4 |
| | 1 | 21 | 22.4 | 22.9 | 23 | 23.3 | 22.7 | 22.3 |
| | 2 | 20.1 | 21.2 | 21.4 | 21.1 | 19.5 | 19.3 | 18.6 |
| | 3 | 20.9 | 21.8 | 23.1 | 22.5 | 23.2 | 23.9 | 24.2 |
| | 4 | 19.9 | 21.1 | 22.3 | 21.7 | 21.7 | 21 | 20.2 |
| PSP dimer 1 µmol | 1 | 23.4 | 23.3 | 24.4 | 23.9 | 23.9 | 24 | 23 |
| | 2 | 19.4 | 20 | 20.7 | 19.6 | 20.1 | 20.7 | 20.7 |
| | 3 | 21.1 | 22.5 | 22.5 | 21.8 | 21.8 | 23.2 | 23.4 |
| | 1 | 22.1 | 22.1 | 23.2 | 22.9 | 23.4 | 22.8 | 21.4 |
| | 2 | 20.2 | 20.8 | 21.5 | 21.6 | 21.3 | 21.1 | 19.4 |
| | 3 | 21.5 | 21.8 | 22.5 | 22.3 | 22.7 | 22.7 | 23 |
| | 4 | 19.8 | 21.1 | 22.5 | 22.4 | 23.1 | 24.1 | 24.5 |
| PSP dimer 10 µmol | 1 | 19.5 | 20.8 | 21.4 | 21.1 | 21.3 | 21 | 20.6 |
| | 2 | 21.9 | 23.3 | 23.9 | 22.6 | 22.3 | 22.4 | 21.7 |
| | 3 | 21.7 | 22.9 | 22.2 | 20.5 | 20.9 | 21.9 | 22 |
| | 1 | 20.2 | 21.2 | 21.7 | 21.2 | 21.2 | 21.7 | 21.1 |
| | 2 | 21 | 21.7 | 22.8 | 21.8 | 21.1 | 21.4 | 21.4 |
| | 3 | 20.6 | 21.1 | 21.3 | 21.4 | 21.1 | 21.5 | 21.9 |
| | 4 | 22 | 23.1 | 23.1 | 22.6 | 22.3 | 23.1 | 22.3 |

TABLE 9

Body weight (g)

| | | Days | | | | | | |
|---|---|---|---|---|---|---|---|---|
| | | 15 | 17 | 20 | 24 | 27 | 31 | 34 |
| Normal | 1 | 22.35 | 22.7 | 22.2 | 22.9 | 23 | 23 | 23.6 |
| | 2 | 22.36 | 22.7 | 22.6 | 23.7 | 22.5 | 23.5 | 21.4 |
| | 3 | 22.45 | 22.7 | 22.6 | 23.6 | 21 | 23.6 | 23 |
| | 4 | 22.78 | 22.7 | 22.4 | 23.7 | 22.8 | 23.3 | 23.6 |
| | 5 | 21.42 | 21.4 | 21.4 | 21.9 | 23.1 | 21.7 | 23.4 |
| PBS | 1 | 18.41 | 18 | 19.4 | 20 | 19.5 | 19.7 | 20 |
| | 2 | 22.5 | 22.5 | 23.2 | 24 | 23.7 | 24.8 | 22.7 |
| | 3 | 22.47 | 22.6 | 22.1 | 23.2 | 22.6 | 22.3 | 21.2 |
| | 4 | 20.43 | 20.7 | 20.7 | 21.2 | 21.5 | 22.2 | 21.3 |
| | 5 | 20.99 | 21.6 | 21.5 | 22 | 21 | 22.1 | 22.2 |
| | 6 | 21.75 | 22.1 | 22 | 22 | 22.8 | 23.1 | 22.4 |
| PSP trimer 0.1 µmol | 1 | 20.75 | 21 | 21.2 | 22.2 | 21.3 | 20.3 | 19.7 |
| | 2 | 20.64 | 20.6 | 21.3 | 21.7 | 21.4 | 21.3 | 20.5 |
| | 3 | 21.54 | 21.5 | 20.8 | 22.6 | 22.7 | 21 | 19.8 |
| | 1 | 19.43 | 19.1 | 19.6 | 19.9 | 19.5 | 18.6 | 18.1 |
| | 2 | 22.27 | 22.3 | 22.9 | 23.8 | 23.6 | 24.3 | 24.1 |
| | 3 | 20.75 | 21.3 | 21.9 | 22.8 | 22.2 | 23.3 | 23 |
| | 4 | 21.68 | 21.7 | 21.7 | 21.9 | 21.8 | 21 | 21.3 |
| PSP trimer 1 µmol | 1 | 20.76 | 21.5 | 22.3 | 23.2 | 22.3 | 21.4 | 20.1 |
| | 2 | 21.15 | 21.1 | 21.6 | 22.6 | 22.4 | 22.7 | 22.6 |
| | 3 | 21.62 | 22.2 | 22.9 | 23.8 | 23.8 | 22.8 | 21.1 |
| | 1 | 21.02 | 21.7 | 22.1 | 22.7 | 22.8 | 22.5 | 19.9 |
| | 2 | 20.4 | 21.3 | 21.8 | 22.7 | 22.6 | 21.4 | 20.7 |
| | 3 | 21.15 | 21.5 | 20.8 | 21.3 | 21.5 | 21.7 | 22 |
| | 4 | 19.02 | 19.1 | 19.2 | 20.2 | 19.8 | 19.9 | 19.3 |
| PSP trimer 10 µmol | 1 | 21.9 | 21.2 | 21.1 | 22.5 | 21.9 | 22.5 | 22.7 |
| | 2 | 23.39 | 23 | 23.2 | 23.8 | 23.1 | 23.9 | 23.9 |
| | 3 | 21.077 | 22.5 | 23 | 24 | 23.7 | 24.1 | 24.3 |
| | 1 | 20.1 | 21 | 21.3 | 22.4 | 22.5 | 21.9 | 20.8 |
| | 2 | 18.84 | 19 | 19.7 | 20.2 | 20.8 | 21.2 | 20.8 |
| | 3 | 20.59 | 20.7 | 22.7 | 22.9 | 22.3 | 22.5 | 22 |
| | 4 | 22.15 | 22.9 | 22.9 | 23 | 22.8 | 22.6 | 22.4 |

The aforementioned description of the present invention is to be exemplified, and it can be understood by those skilled in the art that the technical spirit or required features of the present invention can be easily modified in other detailed forms without changing. Therefore, it should be understood that the above-described exemplary embodiments are illustrative in all aspects and do not limit the present invention.

The invention claimed is:

1. A peptide selected from the group consisting of the amino acid sequence consisting of SEQ ID NO: 1 or the amino acid sequence consisting of SEQ ID NO: 2, wherein the N- or C-terminal of the peptide is attached to a protective group selected from the group consisting of an acetyl group, a fluorenylmethoxy carbonyl group, a formyl group, a palmitoyl group, a myristyl group, a stearyl group or a polyethylene glycol (PEG) group.

2. A method for treating rheumatoid arthritis, comprising the step of administering a composition comprising a pharmaceutically effective amount of a peptide selected from the group consisting of the amino acid sequence consisting of SEQ ID NO: 1 or the amino acid sequence consisting of SEQ ID NO: 2, or a polynucleotide encoding the peptide as an active ingredient to a subject having the arthritis.

3. The method of claim 2, wherein the N- or C-terminal of the peptide is attached to a protective group selected from the group consisting of an acetyl group, a fluorenylmethoxy carbonyl group, a formyl group, a palmitoyl group, a myristyl group, a stearyl group or a polyethylene glycol (PEG) group.

4. The method of claim 2, wherein the composition inhibits generation of inflammatory cytokine.

5. The method of claim4, wherein the inflammatory cytokine is interleukin-18 (IL-18).

6. The method of claim 2, wherein the composition further comprises a pharmaceutically acceptable carrier.

7. The method of claim 2, wherein the composition is simultaneously, separately or sequentially administered with other anti-inflammatory agents in addition to the peptide selected from the group consisting of the amino acid sequence consisting of SEQ ID NO: 1 or the amino acid sequence consisting of SEQ ID NO: 2 or the polynucleotide encoding the peptide.

8. The method of claim 2, wherein the composition is formulated for oral administration, intramuscular administration, intravenous administration, intraperitoneal administration, subcutaneous administration, intradermal administration, or topical administration.

* * * * *